United States Patent
Shen

(10) Patent No.: US 11,787,790 B2
(45) Date of Patent: Oct. 17, 2023

(54) BENZIMIDAZOLE DERIVATIVE HAVING FLUORINE-CONTAINING SUBSTITUENT, PREPARATION AND APPLICATION THEREOF

(71) Applicant: YUNBAIYAO ZHENGWU SCIENCE AND TECHNOLOGY (SHANGHAI) CO., LTD., Shanghai (CN)

(72) Inventor: Zhengwu Shen, Shanghai (CN)

(73) Assignee: YUNBAIYAO ZHENGWU SCIENCE AND TECHNOLOGY (SHANGHAI) CO., LTD., Shanghai (CN)

( * ) Notice: Subject to any disclaimer, the term of this patent is extended or adjusted under 35 U.S.C. 154(b) by 0 days.

(21) Appl. No.: 17/947,260

(22) Filed: Sep. 19, 2022

(65) Prior Publication Data

US 2023/0040251 A1 Feb. 9, 2023

Related U.S. Application Data

(63) Continuation of application No. PCT/CN2021/077769, filed on Feb. 25, 2021.

(30) Foreign Application Priority Data

Apr. 26, 2020 (CN) .......................... 202010338743.5

(51) Int. Cl.
*C07D 413/04* (2006.01)
*A61P 35/00* (2006.01)
*A61K 45/06* (2006.01)

(52) U.S. Cl.
CPC ............ *C07D 413/04* (2013.01); *A61K 45/06* (2013.01); *A61P 35/00* (2018.01)

(58) Field of Classification Search
CPC ................................ C07D 413/04; A61P 35/00
See application file for complete search history.

(56) References Cited

FOREIGN PATENT DOCUMENTS

| CN | 108139405 A | 6/2018 |
|---|---|---|
| CN | 111454254 A | 7/2020 |
| WO | 03066629 A2 | 8/2003 |
| WO | 2004103994 A1 | 12/2004 |
| WO | 2011012577 A1 | 2/2011 |
| WO | 2012050365 A9 | 6/2012 |
| WO | 2017068182 A1 | 4/2017 |

OTHER PUBLICATIONS

Wolff, Manfred E. "Burger's Medicinal Chemistry, 5ed, Part I", John Wiley & Sons, 1995, pp. 975-977.*
Golub et al. Science, vol. 286, Oct. 15, 1999, pp. 531-537.*
Zhang Haixia et al., New Oral Antitumor Drug_Temozolomide, Foreign Medical Sciences: Cancer Section, 1999, 26(5): 292-293.
Zhao Caixia et al., Research on Temozolomide in Cerebral Neurogliocytoma, Clinical Misdiagnosis & Mistherapy, 2009, 22(3): 70-73, PLA Bethune International Peace Hospital, Shijiazhuang, 050082.
Lashford, L. S et al., Temozolomide in Malignant Gliomas of Childhood: A United Kingdom Children's Cancer Study Group and French Society for Pediatric Oncology Intergroup Study. Journal of Clinical Oncology, 20(24), 4684-4691.
Zhu Zhengquan et al.,Clinical efficacy of Temozolomide ( TMZ) used for high-grade gliomas in 34 patients, Chinese Journal of Modern Drug Application, 2011 Issue 18, pp. 6-7, Cancer Hospital of Xinjiang Medical University, Xinjiang 830011, China.

* cited by examiner

*Primary Examiner* — Samira J Jean-Louis

(57) ABSTRACT

Disclosed are a benzimidazole derivative of formula (I), or an isomer, a pharmaceutically-acceptable salt, or a prodrug thereof, and a preparation thereof. An application of the benzimidazole derivative in the treatment of tumors is further provided.

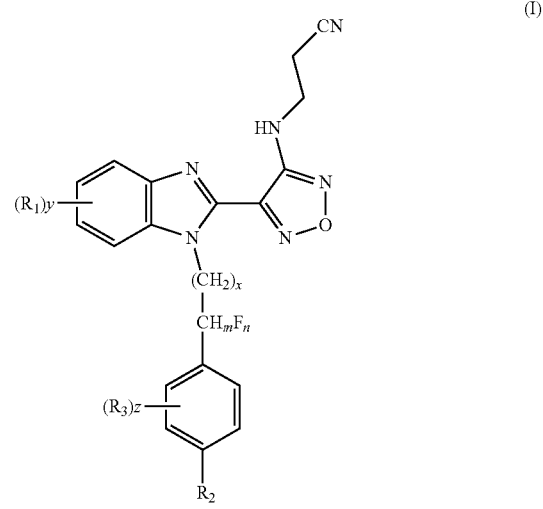

10 Claims, No Drawings

BENZIMIDAZOLE DERIVATIVE HAVING FLUORINE-CONTAINING SUBSTITUENT, PREPARATION AND APPLICATION THEREOF

CROSS-REFERENCE TO RELATED APPLICATIONS

This application is a continuation of International Patent Application No. PCT/CN2021/077769, filed on Feb. 25, 2021, which claims the benefit of priority from Chinese Patent Application No. 202010338743.5, filed on Apr. 26, 2020. The content of the aforementioned application, including any intervening amendments thereto, is incorporated herein by reference in its entirety.

TECHNICAL FIELD

This application relates to pharmaceutical chemistry, and more specifically to a benzimidazole derivative having a fluorine-containing substituent, and a preparation and application thereof.

BACKGROUND

Due to the aggravated aging of the population, the destruction of ecological environment, the development of unhealthy lifestyle, and the occurrence of food safety problems, the cancer incidence has continued to rise over years in China, and has become a public health problem, even a social problem, which must be highly focused on. As predicted by the International Cancer Research Agency, if no effective measures are taken, the number of cancer cases and the number of cancer deaths in China will rise to 4 million and 3 million in 2020, and 5 million and 3.5 million in 2030, respectively.

Brain tumor is relatively special among the clinical tumor diseases, which is treated in clinic mainly by surgery since most chemotherapeutic drugs cannot cross the blood-brain barrier and thus are practically ineffective for the treatment of brain tumors. Temozolomide is a novel oral administrated anti-tumor drug with broad-spectrum anti-tumor activity and has a bioavailability of nearly 100%. Most important, temozolomide can cross the blood-brain barrier, thus was used as the first-line treatment of glioblastoma and mesenchymal astrocytoma (Foreign Medical Sciences: Cancer Section, 1999, 26 (5): 292-293; *Clinical Misdiagnosis & Mistherapy,* 2009, 22(3): 70-73). Therefore, currently, the widely recognized treatment strategy of malignant glioma is surgery combined with temozolomide, or a combo of radiotherapy and chemotherapy with temozolomide. Unfortunately, it has been clinically demonstrated that the overall response rate (ORR) of temozolomide against the malignant glioma is lower than 45% (Lashford, L. S., et al. "Temozolomide in malignant gliomas of childhood: a United Kingdom Children's Cancer Study Group and French Society for Pediatric Oncology Intergroup Study." *Journal of Clinical Oncology* 2002, 20(24):4684-91). Moreover, some clinical trials also show that after the surgery, a one-year survival rate of the high-grade glioma patients is merely 32.84% under the treatment of temozolomide alone (Zhou Zhen-quan, Liu Liang, Xia Hai-cheng, et al. "Clinical efficacy of Temozolomide (TMZ) used for high-grade gliomas in 34 patients", *Chinese Journal of Modern Drug Application,* 2011, 5 (18): 6-7). Therefore, it is still urgently needed to develop better drugs for the treatment of brain tumors.

In recent years, 3-{[4-(1-(4-aminoacetophenone)-benzimidazol-2-yl)-1,2,5-oxadiazol-3-yl]amino}propionitrile (11) has been reported is capable of crossing the blood-brain barrier, and thus has the potential to be used for treating glioma (Chinese patent publication No. 108139405A):

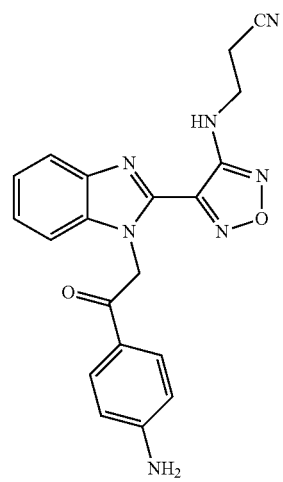

Nevertheless, considering the presence of the 4-aminoacetophenone moiety which attached to the nitrogen atom of benzimidazole through the α-carbon of the ketone, the compound 11 has relatively poor chemical stability, and tends to suffer hydrolysis in vivo. Moreover, the p-aminoacetophenone moiety attenuates the efficiency of the compound to cross the blood-brain barrier, thereby weakening the therapeutic effects against brain tumors.

SUMMARY

An object of this application is to provide a benzimidazole derivative having a fluorine-containing substituent, and a preparation and application thereof to overcome the defects in the prior art.

Technical solutions of this application are described as follows.

In a first aspect, this application provides a benzimidazole derivative of formula (I), or an isomer, a pharmaceutically-acceptable salt, or a prodrug thereof:

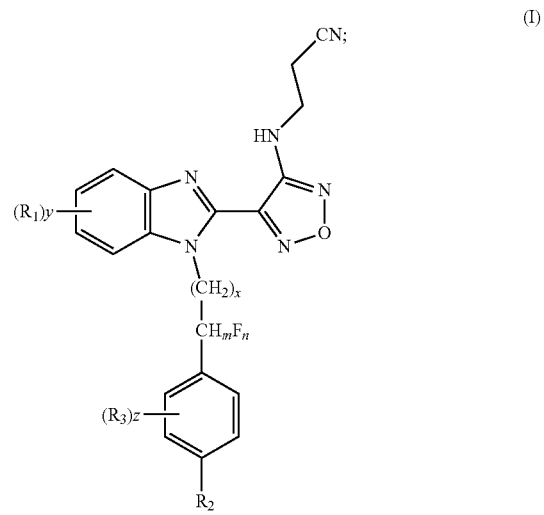

wherein x is 0, 1, or 2;
when m is 0 or 1, n is 1 or 2; when m is 0, n is 2; and when m is 1, n is 1;

y is 0, 1, 2, 3 or 4; $R_1$ is each independently halogen, phenolic hydroxyl or a derivative thereof, carboxyl or a derivative thereof, an amino group or a derivative thereof, a sulfonic acid group or a salt thereof, a phosphoric acid group or a salt thereof, sulfone or a sulphoxide derivative, a $C_1$-$C_{15}$ alkyl group or a derivative thereof, a $C_1$-$C_{15}$ alkenyl or a derivative thereof, a $C_1$-$C_{15}$ alkynyl or a derivative thereof, a $C_5$-$C_8$ aryl or a derivative thereof, naphthyl or a naphthol derivative, or a five-to-eight-membered heterocyclic or fused heterocyclic ring containing 1-4 heteroatoms;

$R_2$ is an amino group or a derivative thereof; and z is 0, 1, 2, 3 or 4; $R_3$ is each independently halogen, phenolic hydroxyl or a derivative thereof, carboxyl or a derivative thereof, an amino group or a derivative thereof, a sulfonic acid group or a salt thereof, a phosphoric acid group or a salt thereof, sulfone or a sulfoxide derivative, a $C_1$-$C_{15}$ alkyl group or a derivative thereof, a $C_1$-$C_{15}$ alkenyl or a derivative thereof, a $C_1$-$C_{15}$ alkynyl or a derivative thereof, a $C_5$-$C_8$ aryl or a derivative thereof, naphthyl or a naphthol derivative, or a five-to-eight-membered heterocyclic or fused heterocyclic ring containing 1-4 heteroatoms.

In some embodiments, x is 0.

In some embodiments, the benzimidazole derivative is selected from the group consisting of:

1

2

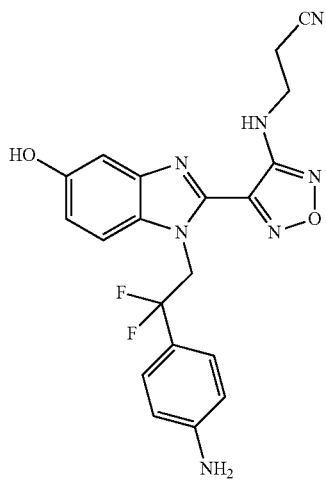

3

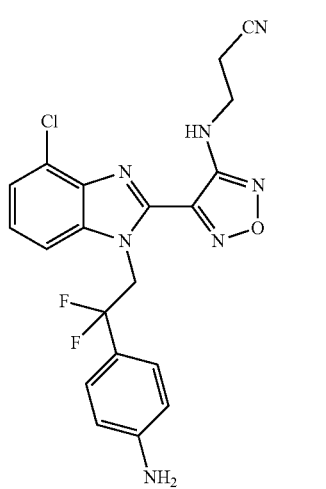

4

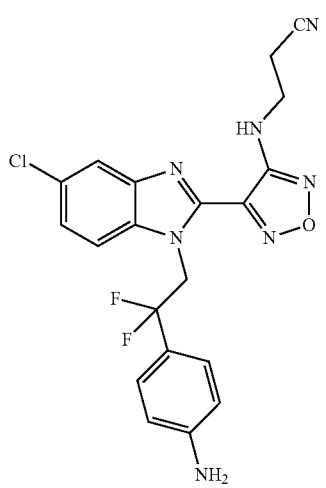

5

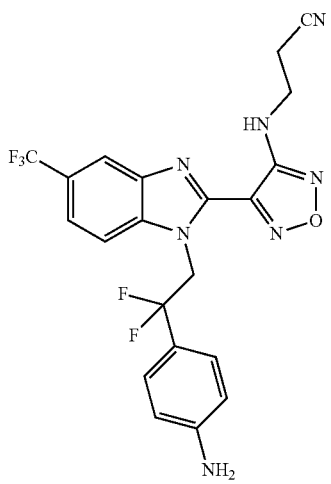

5

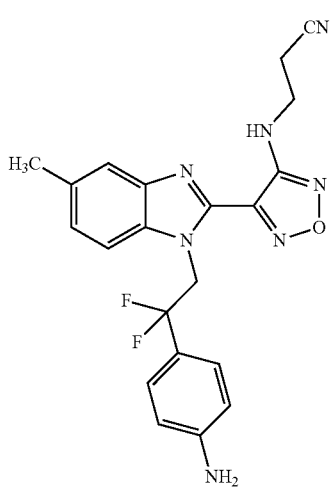

7

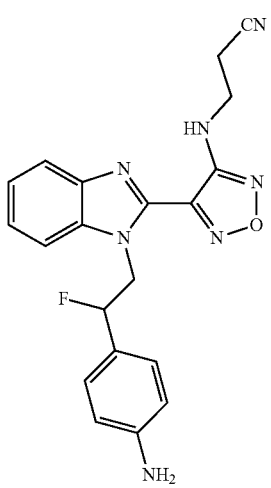

8

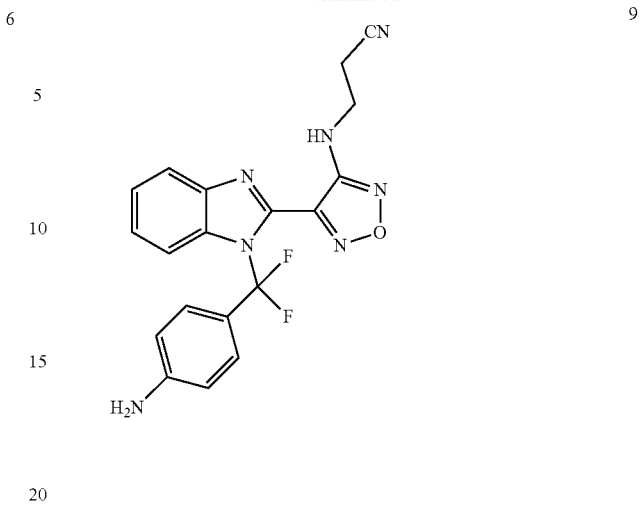

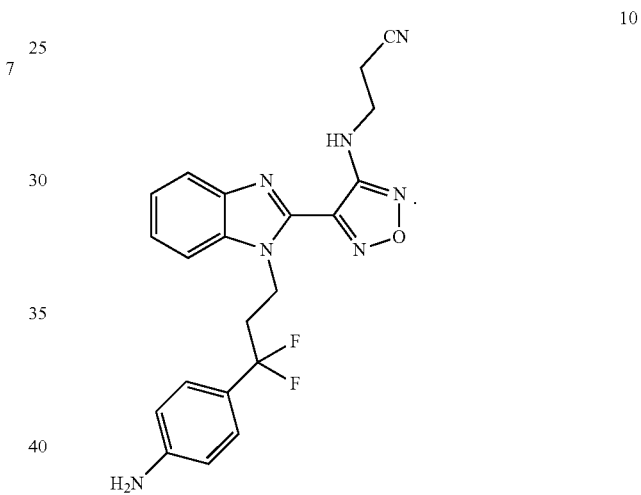

In a second aspect, this application provides a pharmaceutical composition, comprising:

the benzimidazole derivative, or an isomer thereof, or a pharmaceutically acceptable salt thereof, or a prodrug molecule thereof; and a pharmaceutically-acceptable carrier, a pharmaceutically-acceptable diluent, a pharmaceutically-acceptable excipient, or a combination thereof.

In a third aspect, this application provides a method of preparing the benzimidazole derivative, comprising:

(1) reacting compound (a) with acrylonitrile followed by purification to form compound (b);

(2) reacting the compound (b) with compound (c) in a first solvent in the presence of a base followed by purification to obtain compound (d);

(3) subjecting the compound (d) to fluorination in a second solvent in the presence of a fluorinating agent followed by purification to obtain compound (e), wherein the fluorinating agent is diethylaminosulfur trifluoride (DAST) or bis (2-methoxyethyl) aminosulfur trifluoride (BAST); and (4) converting $R_2'$ in the compound (e) into $R_2$ in a third solvent followed by purification to obtain compound (I-1), as shown in the following reaction scheme:

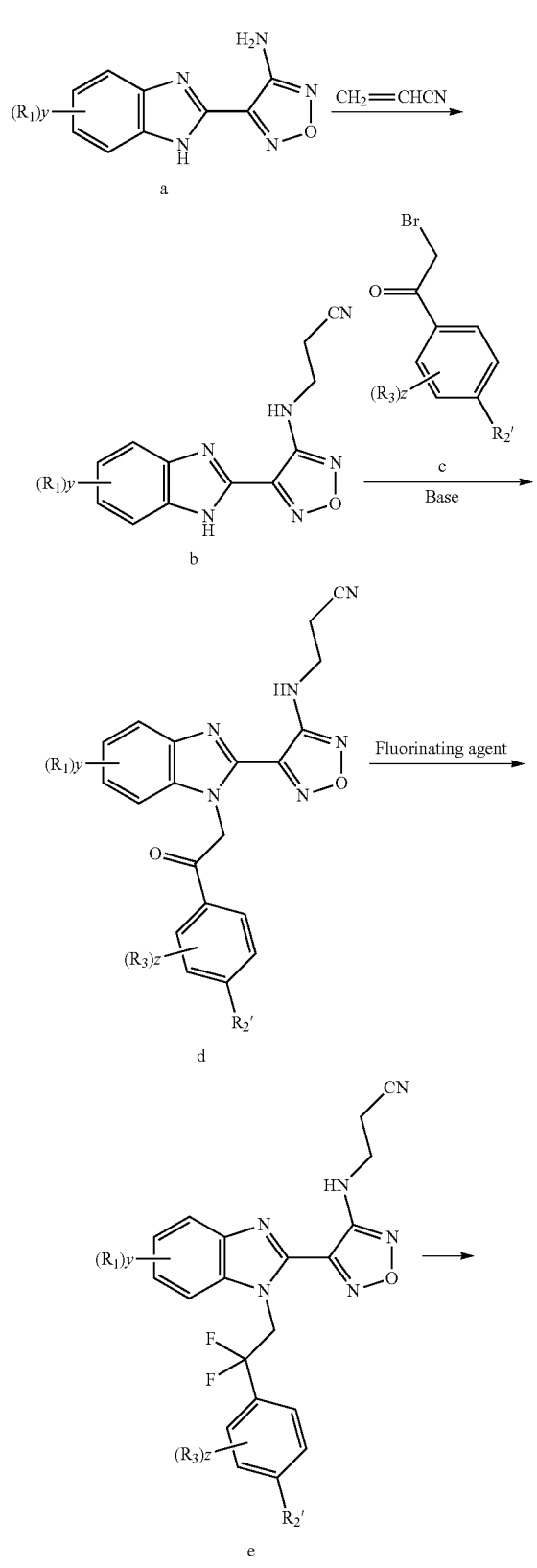

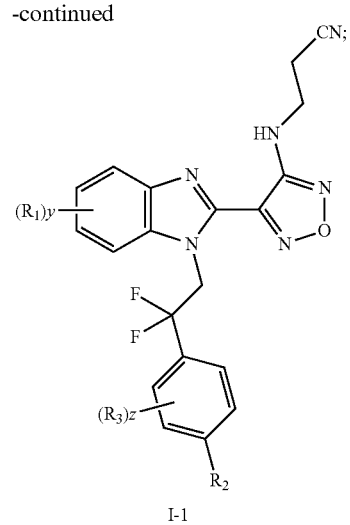

wherein $R_2'$ is nitro group or a protected amino group;

the base is an inorganic base or an organic base; wherein the inorganic base is selected from the group consisting of sodium hydroxide, potassium hydroxide, sodium hydride, calcium hydride, calcium fluoride, cesium fluoride, sodium carbonate, potassium carbonate, cesium carbonate, potassium phosphate and a combination thereof; and the organic base is selected from the group consisting of lithium diisopropylamide, butyl lithium, lithium bis(trimethylsilyl)amide, triethylamine, diisopropylethylamine, 1,8-diazabicyclo[5.4.0]undec-7-ene and a combination thereof;

the first solvent, the second solvent and the third solvent are independently a proton solvent, an aprotic solvent, or a mixture thereof;

steps (1)-(4) are independently performed at a temperature of −78-180° C.;

purifications in steps (1)-(4) are performed each independently by solvent extraction, precipitation, crystallization, column chromatography or a combination thereof; and in the column chromatography, a filler is gel, macro porous resin, or aluminum oxide; and an eluent is a petroleum ether-acetone mixture, a petroleum ether-ethyl acetate mixture, or a petroleum ether-dichloromethane mixture.

In some embodiments, the first solvent, the second solvent and the third solvent are each independently dichloromethane, dichloroethane, tetrahydrofuran, acetonitrile, ethylene glycol dimethyl ether, N, N-dimethylformamide, or dimethyl sulfoxide.

In a fourth aspect, this application provides a method of preparing the benzimidazole derivative of claim 1, comprising:

(1) reacting compound (b) with compound (c1) in a first solvent in the presence of a base followed by purification to produce compound (e1); and (2) converting $R_2'$ in the compound (e1) into $R_2$ in a second solvent followed by purification to obtain compound (I), as shown in the following reaction scheme:

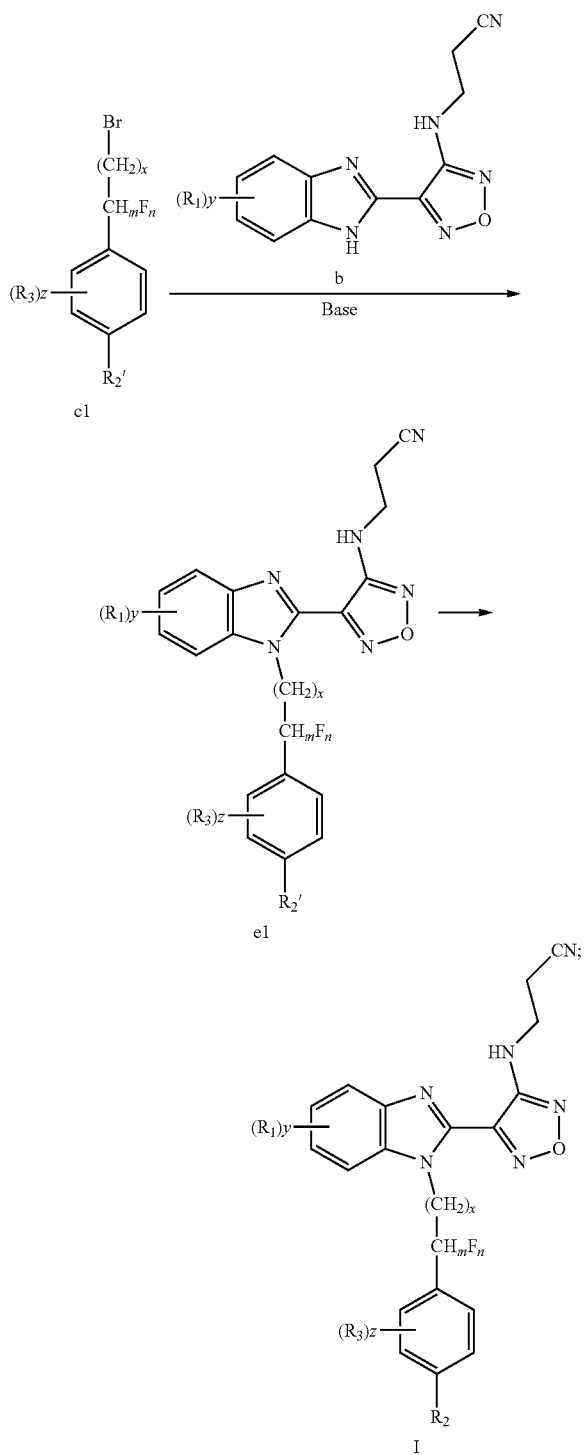

wherein $R_2'$ is nitro group or a protected amino group;
the base is an inorganic base or an organic base; wherein the inorganic base is selected from the group consisting of sodium hydroxide, potassium hydroxide, sodium hydride, calcium hydride, calcium fluoride, cesium fluoride, sodium carbonate, potassium carbonate, cesium carbonate, potassium phosphate and a combination thereof; and the organic base is selected from the group consisting of lithium diisopropylamide, butyl lithium, lithium bis(trimethylsilyl)amide, triethylamine, diisopropylethylamine, 1,8-diazabicyclo [5.4.0]undec-7-ene and a combination thereof;
the first solvent and the second solvent are independently a proton solvent, an aprotic solvent, or a mixture thereof;
steps (1)-(2) are independently performed at a temperature of $-78$-$180°$ C.;
purifications in steps (1)-(2) are performed each independently by solvent extraction, precipitation, crystallization, column chromatography or a combination thereof; and
in the column chromatography, a filler is gel, macro porous resin, or aluminum oxide; and an eluent is a petroleum ether-acetone mixture, a petroleum ether-ethyl acetate mixture, or a petroleum ether-dichloromethane mixture.

In some embodiments, the first solvent and the second solvent are each independently dichloromethane, dichloroethane, tetrahydrofuran, acetonitrile, ethylene glycol dimethyl ether, N, N-dimethylformamide, or dimethyl sulfoxide.

In a fifth aspect, this application provides a method for treating a cancer in a subject in need thereof, comprising:
administering the benzimidazole derivative, or an isomer, a pharmaceutically-acceptable salt, or a prodrug thereof to the subject.

In some embodiments, the cancer is selected from the group consisting of brain cancer, glioma, endometrial cancer, ovarian cancer, cervical cancer, breast cancer, colon cancer, lung cancer, prostate cancer, liver cancer, leukemia, lymphoma, skin cancer, basal cell carcinoma, hemangioma, uterine cancer, laryngeal cancer, gastric cancer, lip cancer, esophageal cancer, nasopharyngeal carcinoma, gallbladder cancer, pancreatic cancer, renal cancer, tongue cancer, bladder cancer, melanoma, lipoma, thyroid cancer, thymic cancer, and bone cancer.

In some embodiments, the benzimidazole derivative, or an isomer, a pharmaceutically-acceptable salt, or a prodrug thereof is administered in combination with an anticancer agent.

In some embodiments, the anticancer agent is selected from the group consisting of adriamycin, bleomycin, vincristine, taxane, etoposide, 5-fluorouracil, cyclophosphamide, methotrexate, cisplatin, retinoic acid, temozolomide, actinomycin, imatinib, gefitinib, sorafenib, erlotinib, sunitinib, afatinib, cabozantinib, Osimertinib, rituximab, cetuximab, trastuzumab, nivolumab, pembrolizumab, atezolizumab, durvalumab, avelumab and a combination thereof.

Compared to the prior art, this application has the following beneficial effects.

(1) The fluorine element is introduced into the molecular structure, and the acetophenone moiety was converted into fluorinated phenylethyl group so that the stability of the compound was improved, and the lipophilicity was increased, thereby making the compound easier to pass through the blood-brain barrier, and greatly improving the anticancer activity of the compound. Therefore, the compound provided herein is promising in the aspect of treating brain glioma.

(2) This application provides a benzimidazole derivative having a fluorine-containing substituent, which has lower toxicity, better stability, and a higher lipophilicity compared with compound 11 and the analogs thereof. Hence, the benzimidazole derivative with the fluorine-containing substituent can be used as a new antitumor agent, which can effectively inhibit the proliferation of various tumor cells. It can pass through the blood-brain barrier and can be used for curing various tumor diseases, such as brain glioma, by a single use or combined use with other related drugs.

DETAILED DESCRIPTION OF EMBODIMENTS

This application will be described in detail below with reference to the embodiments to make objects, technical features and advantages of this application clearer, but these embodiments are not intended to limit the scope of this application. Other embodiments obtained by those skilled in the art based on the content disclosed herein without paying any creative efforts shall fall within the scope of this application.

Example 1 Preparation of Compound 1 (3-[(4-{1-[2-(4-aminophenyl)-2,2-difluoroethyl]-1H-benzimidazol-2-yl}-1,2,5-oxadiazol-3-yl)amino] propionitrile)

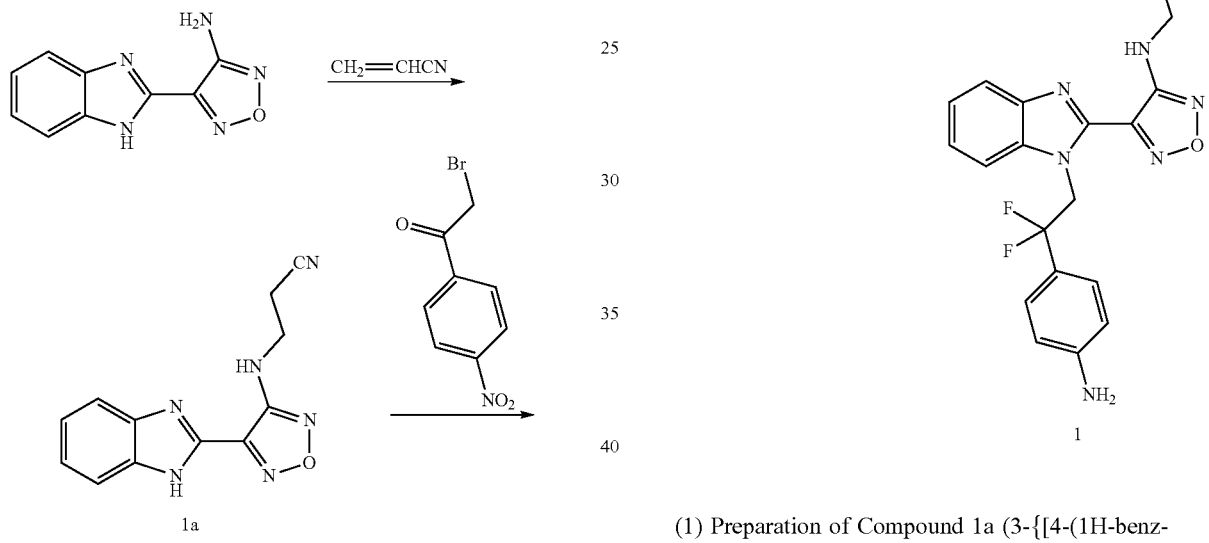

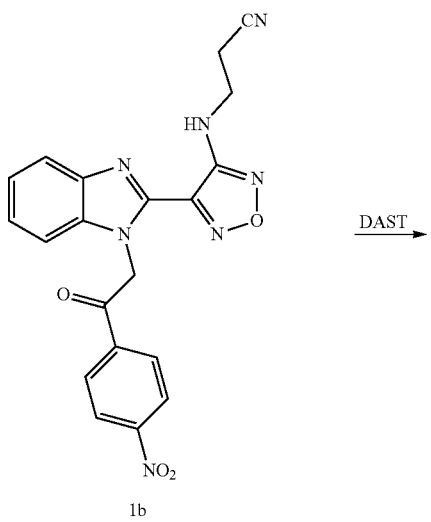

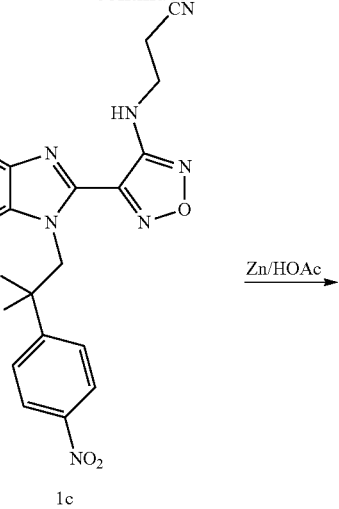

(1) Preparation of Compound 1a (3-{[4-(1H-benzimidazol-2-yl)-1,2,5-oxadiazol-3-yl]amino} propionitrile)

4-(1H-benzimidazol-2-yl)-1,2,5-oxadiazol-3-amine (18.2 g, 90.5 mmol) was dissolved in 240 mL of anhydrous pyridine, cooled in ice water, and sequentially added with 30 mL of a solution of sodium methoxide (8.8 g, 162.9 mmol) in methanol and 6 mL of acrylonitrile (90.5 mmol). The reaction mixture was stirred at 60° C. overnight. After the reaction was confirmed by thin-layer silica gel chromatography to be completed, the reaction mixture was evaporated under reduced pressure, added with 300 mL of water and subjected to extraction three times each with 100 mL of ethyl acetate. The organic phases were combined, washed with 100 mL of saturated NaCl solution, dried with anhydrous sodium sulfate, and concentrated, and the residue was crystallized with ethyl acetate/n-hexane to obtain 15.8 g of compound 1a as white solid (68.7% yield).

MS: [M+1]$^+$=255.1.

$^1$H NMR (400 MHz, DMSO-d$_6$) δ ppm: 13.75 (brs, 1H), 7.81 (broad, 1H), 7.61 (m, 1H), 7.37-7.34 (m, 2H), 7.21 (t, J=6.4 Hz, 1H), 3.68 (q, J=6.4 Hz, 2H), 2.94 (t, J=6.4 Hz, 2H).

(2) Preparation of Compound 1b (3-[(4-{1-[2-(4-nitrophenyl)-2-oxoethyl]-1H-benzimidazol-2-yl}-1,2,5-oxadiazol-3-yl) amino] propionitrile)

Compound 1a (270 mg, 1.1 mmol) was dissolved in 15 mL of anhydrous N, N-dimethylformamide, to which 2-bromo-1-(4-nitrophenyl)-ethanone (260 mg, 1.1 mmol) and potassium carbonate (276 mg, 2.0 mmol) were sequentially added. The reaction mixture was stirred overnight at room temperature. After the starting material was confirmed by thin-layer silica gel chromatography to be completely consumed, the reaction mixture was evaporated under reduced pressure, added with 100 ml of water and subjected to extraction three times each with 50 mL of ethyl acetate. The organic phases were combined, washed with 100 mL of saturated NaCl solution, dried with anhydrous sodium sulfate, and concentrated under reduced pressure to obtain 459 mg of compound 1b as yellow solid (100% yield).

MS: $[M+1]^+=418.1$.

(3) Preparation of Compound 1c (3-[(4-{1-[2,2-difluoro-2-(4-nitrophenyl)ethyl]-1H-benzimidazol-2-yl}-1,2,5-oxadiazol-3-yl)amino] propionitrile)

Compound 1b (417 mg, 1.0 mmol) was dissolved in dichloromethane (50 mL) under the protection of an inert gas, cooled to 0° C. in ice water, and slowly dropwise added with diethylaminosulfur trifluoride (DAST, 1 mL). The reaction mixture was heated to room temperature, and stirred for 12 hours. After the starting material was confirmed by thin-layer silica gel chromatography to be completely consumed, the reaction mixture was quenched with water (50 mL), and the aqueous layer was separated followed by extraction twice each with 30 mL of dichloromethane. The organic phases were combined, dried with anhydrous sodium sulfate, concentrated and purified by silica gel column chromatography (eluent: a mixture of ethyl acetate and petroleum ether in a volume ratio of 2:3) to obtain 140 mg of intermediate 1c (33.0% yield).

MS: $[M+1]^+=440.1$.

$^1$H NMR (400 MHz, CDCl$_3$) δ ppm: 8.17 (d, J=8.4 Hz, 2H), 7.80 (d, J=8.0 Hz, 1H), 7.50-7.53 (m, 3H), 7.30-7.49 (m, 3H), 5.29 (t, J=13.6 Hz, 2H), 3.69 (m, 2H), 2.77 (t, J=6.4 Hz, 2H).

(4) Preparation of Compound 1 (3-[(4-{1-[2-(4-aminophenyl)-2,2-difluoroethyl]-1H-benzimidazol-2-yl}-1,2,5-oxadiazol-3-yl)amino] propionitrile)

A solution of compound 1c (140 mg, 0.34 mmol) in dichloromethane (20 mL) was sequentially added with glacial acetic acid (1 mL) and zinc powder (150 mg) at room temperature. The reaction mixture was stirred at room temperature for 4 hours. When displayed that the starting material was confirmed by the thin-layer silica gel chromatography to be completely consumed, the reaction mixture was filtered to remove insoluble substances, and concentrated, and the residue was purified by Prep-HPLC to obtain 75 mg of compound 1 as yellow solid (56.0% yield), where the mobile phase was a mixture of acetonitrile and 0.01% aqueous ammonia.

MS: $[M+1]^+=410.1$.

$^1$H NMR (400 MHz, DMSO-d$_6$) δ ppm: 7.86 (d, J=8.8 Hz, 2H), 7.40-7.50 (m, 3H), 7.16 (d, J=8.4 Hz, 2H), 6.60 (d, J=8.4 Hz, 2H), 5.56 (brs, 2H), 5.44 (t, J=14.8 Hz, 2H), 3.67 (m, 2H), 2.94 (t, J=6.8 Hz, 2H).

Similarly, compounds 2-7 were prepared, and corresponding mass spectrometry and NMR data were shown in Table 1.

TABLE 1

| | Mass spectrum and $^1$H NMR data of compounds 2-7 | | |
|---|---|---|---|
| Compounds | Structural formula | MS: $[M + 1]^+$ | $^1$H NMR (400 MHz, DMSO-d$_6$) δ ppm: |
| 2 | [structure] | 426.1 | 9.62 (s, 1H), 7.69 (d, J = 8.4 Hz, 1H), 7.49 (m, 1H), 7.29 (m, 1H), 7.17 (d, J = 8.4 Hz, 2H), 6.93 (d, J = 8.4 Hz, 1H), 6.61 (d, J = 8.4 Hz, 2H), 5.51 (brs, 2H), 5.40 (t, J = 14.8 Hz, 2H), 3.66 (m, 2H), 2.92 (t, J = 6.8 Hz, 2H). |

TABLE 1-continued

Mass spectrum and $^1$H NMR data of compounds 2-7

| Compounds | Structural formula | MS: [M + 1]$^+$ | $^1$H NMR (400 MHz, DMSO-d$_6$) δ ppm: |
|---|---|---|---|
| 3 | (structure) | 426.1 | 9.35 (s, 1H), 7.69 (d, J = 8.4 Hz, 1H), 7.50 (m, 1H), 7.33 (d, J = 2.0 Hz, 1H), 7.16 (d, J = 8.4 Hz, 2H), 6.85 (dd, J = 8.4 Hz, 2.0 Hz, 1H), 6.60 (d, J = 8.4 Hz, 2H), 5.50 (brs, 2H), 5.46 (t, J = 14.8 Hz, 2H), 3.68 (m, 2H), 2.95 (t, J = 6.8 Hz, 2H). |
| 4 | (structure) | 444.1 | 7.74 (d, J = 8.4 Hz, 1H), 7.50 (m, 1H), 7.12-7.20 (m, 3H), 7.07 (m, 1H), 6.60 (d, J = 8.4 Hz, 2H), 5.53 (brs, 2H), 5.45 (t, J = 14.8 Hz, 2H), 3.66 (m, 2H), 2.93 (t, J = 6.8 Hz, 2H). |
| 5 | (structure) | 444.1 | 7.70-7.90 (m, 2H), 7.50 (m, 1H), 7.49 (m, 1H), 7.14 (d, J = 8.4 Hz, 2H), 6.58 (d, J = 8.4 Hz, 2H), 5.54 (brs, 2H), 5.42 (t, J = 14.8 Hz, 2H), 3.67 (m, 2H), 2.92 (t, J = 6.8 Hz, 2H). |

TABLE 1-continued

Mass spectrum and $^1$H NMR data of compounds 2-7

| Compounds | Structural formula | MS: [M + 1]$^+$ | $^1$H NMR (400 MHz, DMSO-d$_6$) δ ppm: |
|---|---|---|---|
| 6 | | 478.1 | 8.02 (d, J = 2.0 Hz, 1H), 7.86 (d, J = 8.4 Hz, 1H), 7.68 (dd, J = 8.4 Hz, 2.0 Hz, 1H), 7.50 (m, 1H), 7.15 (d, J = 8.4 Hz, 2H), 6.62 (d, J = 8.4 Hz, 2H), 5.55 (brs, 2H), 5.43 (t, J = 14.8 Hz, 2H), 3.65 (m, 2H), 2.92 (t, J = 6.8 Hz, 2H). |
| 7 | | 424.2 | 7.70 (d, J = 8.4 Hz, 1H), 7.63 (d, J = 2.0 Hz, 1H), 7.50 (m, 1H), 7.19 (dd, J = 8.4 Hz, 2.0 Hz, 1H), 7.16 (d, J = 8.4 Hz, 2H), 6.60 (d, J = 8.4 Hz, 2H), 5.55 (brs, 2H), 5.43 (t, J = 14.8 Hz, 2H), 3.67 (m, 2H), 2.95 (t, J = 6.8 Hz, 2H), 2.39 (s, 3H). |

Example 2 Preparation of Compound 8 (3-[(4-{1-[2-(4-aminophenyl)-2-fluoroethyl]-1H-benzimidazol-2-yl}-1,2,5-oxadiazol-3-yl) amino] propionitrile)

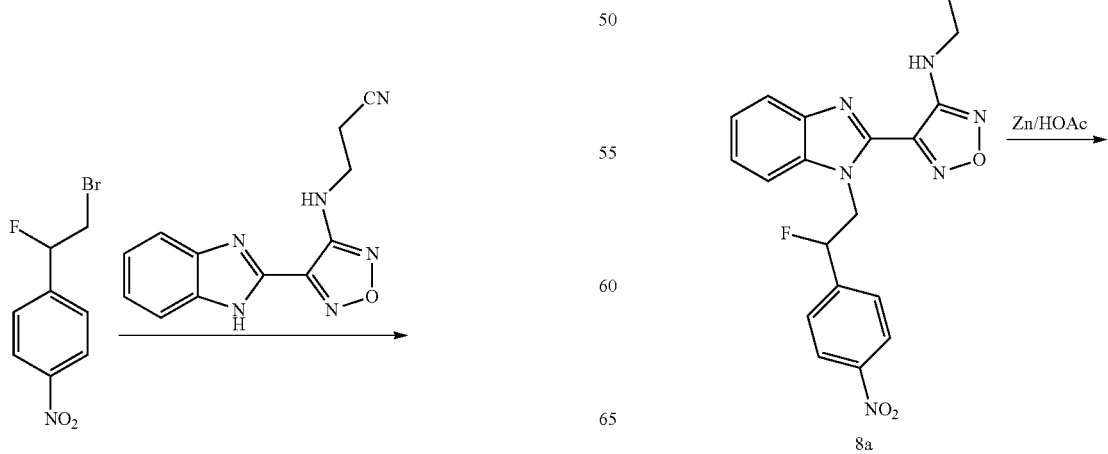

8a

-continued

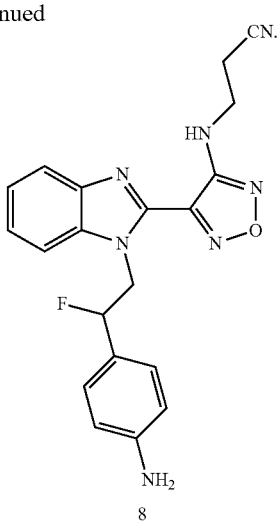

8

(1) Preparation of Compound 8a (3-[(4-{1-[2-fluoro-2-(4-nitrophenyl)ethyl]-1H-benzimidazol-2-yl}-1,2,5-oxadiazol-3-yl)amino] propionitrile)

To a reaction flask were sequentially added 1-(2-bromo-1-fluoroethyl)-4-nitrobenzene (496 mg, 2.0 mmol), potassium carbonate (280 mg, 2.0 mmol), 3-{[4-(1H-benzimidazole-2-yl)-1,2,5-oxadiazol-3-yl]amino} propanenitrile (254 mg, 1.0 mmol), and anhydrous N, N-dimethylformamide (20 mL) to obtain a reaction mixture. The reaction mixture was stirred at 80° C. under for 4 hours, and filtered to remove insoluble substances. After that, the filtrate was diluted with 200 ml of ethyl acetate and washed with water for three times and saturated brine for once. The organic phase was dried with anhydrous sodium sulfate, and concentrated. The residue was purified by silica gel column chromatography (eluent: ethyl acetate/petroleum ether=2/3) to obtain 160 mg of intermediate compound 8a, (38.0% yield).

MS: [M+1]$^+$=422.1

$^1$H NMR (400 MHz, CDCl$_3$) δ ppm: 8.15 (d, J=8.4 Hz, 2H), 7.78 (d, J=8.4 Hz, 1H), 7.45-7.51 (m, 3H), 7.25-7.45 (m, 3H), 5.20 (m, 1H), 4.25 (m, 2H), 3.65 (m, 2H), 2.76 (t, J=6.4 Hz, 2H).

(2) Preparation of compound 8 (3-[(4-{1-[2-(4-aminophenyl)-2-fluoroethyl]-1H-benzimidazol-2-yl}-1,2,5-oxadiazol-3-yl) amino] propionitrile)

A dichloromethane solution (20 mL) of compound 8a (160 mg, 0.38 mmol) was sequentially added with glacial acetic acid (1 mL) and zinc powder (180 mg) at room temperature, and then stirred at room temperature for 4 hours to obtain a reaction mixture. After the starting material was confirmed by thin-layer silica gel chromatography to be completely consumed, the reaction mixture was filtered to remove insoluble substances, and concentrated to remove the solvent. After that, the residue was purified by Prep-HPLC to obtain 80 mg of compound 8 as yellow solid (54.0% yield), where the mobile phase used in Prep-HPLC was a mixture of acetonitrile and water, or a mixture of acetonitrile and 0.01% aqueous ammonia.

MS: [M+1]$^+$=392.1

1H NMR (400 MHz, DMSO-d$_6$) δ ppm: 7.84 (d, J=8.4 Hz, 2H), 7.39-7.50 (m, 3H), 7.14 (d, J=8.4 Hz, 2H), 6.58 (d, J=8.4 Hz, 2H), 5.92 (m, 1H), 5.40 (brs, 2H), 4.50 (m, 2H), 3.99 (m, 1H), 3.65 (m, 2H), 2.93 (t, J=6.8 Hz, 2H).

Compounds 9-10 were obtained by similar methods for synthesizing compound 8, and corresponding spectrogram data were shown in Table 2.

TABLE 2

The mass spectrum and $^1$H NMR data of compounds 9-10

| Compounds | Structural formula | MS: [M + 1]$^+$ | $^1$H NMR (400 MHz, DMSO-d$_6$) δ ppm: |
|---|---|---|---|
| 9 | | 396.1 | 7.80-8.01 (m, 4H), 7.40-7.60 (m, 3H), 6.84 (d, J = 8.8 Hz, 2H), 6.53 (brs, 2H), 3.71 (m, 2H), 2.98 (t, J = 6.8 Hz, 2H) |

TABLE 2-continued

The mass spectrum and $^1$H NMR data of compounds 9-10

| Compounds | Structural formula | MS: [M + 1]$^+$ | $^1$H NMR (400 MHz, DMSO-d$_6$) δ ppm: |
|---|---|---|---|
| 10 | | 424.2 | 7.62-7.83 (m, 4H), 7.24-7.47 (m, 3H), 6.53 (d, J = 8.4 Hz, 2H), 6.38 (brs, 2H), 3.81 (m, 2H), 3.62 (m, 2H), 2.90 (t, J = 6.8 Hz, 2H), 2.45(m, 2H) |

Example 3 Calculation of C log P Values of Compounds 1-11

The C log P value refers to a logarithmic value of the ratio of the distribution coefficient of a substance in n-octanol (oil) to that in water, reflecting the distribution condition of the substance in the oil and water phases. The larger the c log P value, the more lipophilic the substance was, otherwise, the smaller the c log P value, the more hydrophilic the substance was, and the better the water solubility. The dissolution, absorption, distribution, and transport of a drug in vivo were related to the hydrophilia and lipophilia of the drug, that is, the oil-water distribution coefficient c log P. The c log P values of compounds 1-11 prepared herein were calculated by an online tool (http://www.vcclab.org/lab/alogps/) provided by Virtual Computational Chemistry Laboratory (VCCLAB), as shown in Table 3.

TABLE 3 clogP values of compounds 1-11

| | Compounds | | | | | | | | | | |
|---|---|---|---|---|---|---|---|---|---|---|---|
| | 1 | 2 | 3 | 4 | 5 | 6 | 7 | 8 | 9 | 10 | 11 |
| clogP | 3.38 | 2.97 | 2.97 | 3.97 | 3.97 | 4.20 | 3.72 | 3.17 | 3.44 | 3.54 | 2.57 |

Table 3 shows that the c log P values of the compounds 1-10 were all higher than that of the compound 11, indicating that the compounds 1-10 had better lipophilia.

Example 4 Inhibitory Effects of Compounds 1-11 on the Proliferation of Tumor Cells Experimental Purposes The anti-proliferation activities of compounds 1-11 to U87MG cells (human malignant glioma cells, ATCC 5018014), NCI-H1975 cells (human non-small cell lung adenocarcinoma cells, ATCC 57849016), A549 cells (human non-small cell lung cancer cells, ATCC 7503618), HCT 116 (human colon cancer cells, ATCC 4587576), and MCF-7 (human breast cancer cells, ATCC 5105360) were verified by using a CCK-8 method.

Experimental Method

A sample stock solution with a concentration of 20 μM was prepared first. The stock solution was sequentially diluted to obtain 10 samples with concentrations of 20000 nM, 4000 nM, 800 nM, 160 nM, 32 nM, 6.4 nM, 1.28 nM, 0.256 nM, 0.0512 nM, and 0.01024 nM, respectively.

50 μL of cell suspension with density of 2*10$^4$ cells/mL was prepared in 96-well plates followed by pre-culturing in the incubator for 24 hours (37° C., 5% CO$_2$). 50 μL of afore-mentioned sample solution was added into each well. After incubated for 72 hours, 10 μl of CCK-8 solution was added into each well, and then further incubated for additional 2 hours. The OD value was measured at the wavelength of 450 nm with a full-automatic ELISA instrument, and the data was processed by GraphPad Prism 7 to calculate IC$_{50}$.

The experimental results were shown in Table 4.

TABLE 4

IC$_{50}$ values of compounds 1-11 regarding inhibitory effect on proliferation of various tumor cells

| Compounds | U87MG cell IC$_{50}$(μM) | NCI-H1975 cell IC$_{50}$(μM) | A549 cell IC$_{50}$(μM) | HCT116 cell IC$_{50}$(μM) | MCF-7 cell IC$_{50}$(μM) |
|---|---|---|---|---|---|
| 1 | 0.0313 | 0.0194 | 0.0290 | 0.0197 | 0.0330 |
| 2 | 0.0224 | 0.0312 | 0.0182 | 0.0283 | 0.0174 |

TABLE 4-continued

IC$_{50}$ values of compounds 1-11 regarding inhibitory effect on proliferation of various tumor cells

| Compounds | U87MG cell IC$_{50}$(μM) | NCI-H1975 cell IC$_{50}$(μM) | A549 cell IC$_{50}$(μM) | HCT116 cell IC$_{50}$(μM) | MCF-7 cell IC$_{50}$(μM) |
|---|---|---|---|---|---|
| 3 | 0.0132 | 0.0133 | 0.0268 | 0.0136 | 0.0132 |
| 4 | 0.0273 | 0.0149 | 0.0129 | 0.0121 | 0.0217 |
| 5 | 0.0157 | 0.0274 | 0.0132 | 0.0358 | 0.0169 |
| 6 | 0.0342 | 0.0119 | 0.0147 | 0.0172 | 0.0132 |
| 7 | 0.0125 | 0.0324 | 0.0139 | 0.0137 | 0.0257 |
| 8 | 0.0156 | 0.0175 | 0.0337 | 0.0244 | 0.0228 |
| 9 | 0.0239 | 0.0198 | 0.0287 | 0.0285 | 0.0328 |
| 10 | 0.0412 | 0.0343 | 0.0415 | 0.0387 | 0.0385 |
| 11 | 0.0512 | 0.0428 | 0.0424 | 0.0526 | 0.0392 |

The results showed that for the five tested tumor cells, the inhibitory proliferation activity of the compounds 1-10 in vitro were all higher than that of the reference compound 11.

Example 5 Determination of Half-Lethal Dose (LD$_{50}$)

Experimental Purpose

The toxicities of compounds 1-11 were evaluated by measuring the half-lethal dose (LD$_{50}$).

Experimental Method

The SPF-grade Kunming mice, belonging to the outbred stock and weighing 20±2 g, were selected (a ratio of the males to the females was 1:1). The dosage range of each compound was explored through pre-experiments. After that, formal tests were carried out. In the range of 0-100% of the lethal dose obtained by the pre-experiments, five doses were selected to increase or decrease according to the isobaric series to allow the mortality of one half of the groups to be 50% or above, and the other half to be 50% or less. After animal grouping and dosage calculation were completed, gastric administration was performed according to the group. The time from the administration to the beginning of the occurrence of toxic reaction, the poisoning phenomenon and the occurrence sequence thereof, the time of the first occurrence of death, the time of death concentration, and the time of the last occurrence of death were recorded. The number of deaths in each group was recorded day by day. The LD$_{50}$ was calculated according to the test results by using a Bliss calculation method, and the results were shown in Table 5.

TABLE 5

Half-lethal dose (LD$_{50}$) of compounds 1-11 for mice

| | Compounds | | | | | | | | | | |
|---|---|---|---|---|---|---|---|---|---|---|---|
| | 1 | 2 | 3 | 4 | 5 | 6 | 7 | 8 | 9 | 10 | 11 |
| LD$_{50}$(mg/KG) | 267 | 245 | 239 | 262 | 264 | 254 | 239 | 291 | 305 | 323 | 153 |

The results showed that the half-lethal dose LD$_{50}$ values of the compounds 1-10 were higher than that of the compound 11, that was, the toxicity of the compounds 1-10 was lower than that of the compound 11.

The above embodiments are merely illustrative, and are not intended to limit the present disclosure. It should be noted that various modifications and improvements made by one of ordinary skill in the art without departing from the spirit of the present disclosure shall fall within the scope of the present disclosure defined by the appended claims.

What is claimed is:

1. A benzimidazole derivative of formula (I), or an isomer, or a pharmaceutically-acceptable salt thereof:

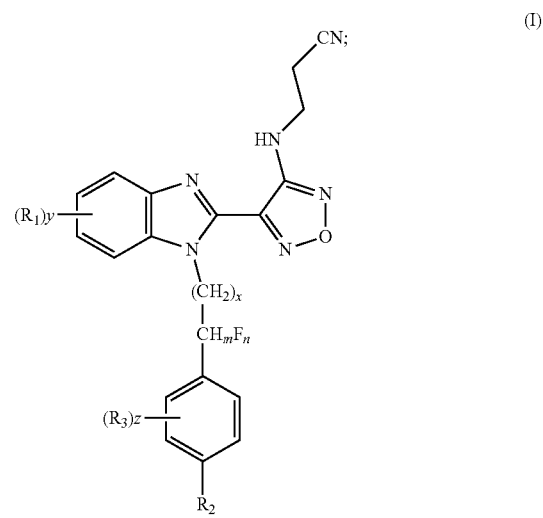

wherein x is 0, 1, or 2;
when m is 0, n is 2; and when m is 1, n is 1;
y is 0, 1, 2, 3 or 4; $R_1$ is each independently halogen, phenolic hydroxyl or a derivative thereof, carboxyl or a derivative thereof, an amino group or a derivative thereof, a sulfonic acid group or a salt thereof, a phosphoric acid group or a salt thereof, sulfone or a sulphoxide derivative, a $C_1$-$C_{15}$ alkyl group or a derivative thereof, a $C_1$-$C_{15}$ alkenyl or a derivative thereof, a $C_1$-$C_{15}$ alkynyl or a derivative thereof, a $C_5$-$C_8$ aryl or a derivative thereof, naphthyl or a naphthol derivative, or a five-to-eight-membered heterocyclic or fused heterocyclic ring containing 1-4 heteroatoms;
$R_2$ is an amino group or a derivative thereof; and
z is 0, 1, 2, 3 or 4; $R_3$ is each independently halogen, phenolic hydroxyl or a derivative thereof, carboxyl or a derivative thereof, an amino group or a derivative thereof, a sulfonic acid group or a salt thereof, a phosphoric acid group or a salt thereof, sulfone or a sulfoxide derivative, a $C_1$-$C_{15}$ alkyl group or a derivative thereof, a $C_1$-$C_{15}$ alkenyl or a derivative thereof, a $C_1$-$C_{15}$ alkynyl or a derivative thereof, a $C_5$-$C_8$ aryl or a derivative thereof, naphthyl or a naphthol derivative, or a five-to-eight-membered heterocyclic or fused heterocyclic ring containing 1-4 heteroatoms.

2. The benzimidazole derivative of claim 1, wherein the benzimidazole derivative is selected from the group consisting of:

1
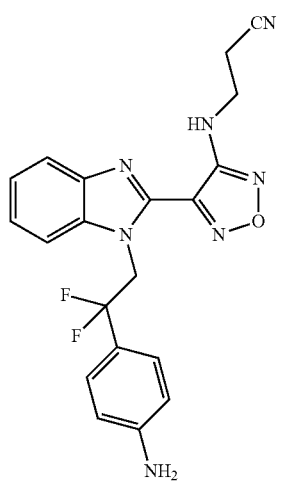
2
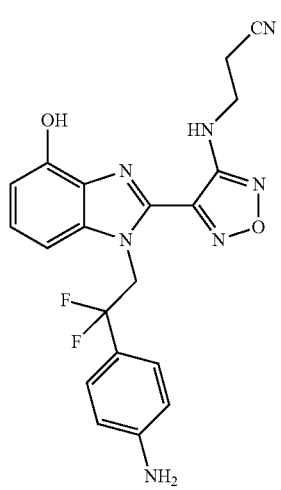
3
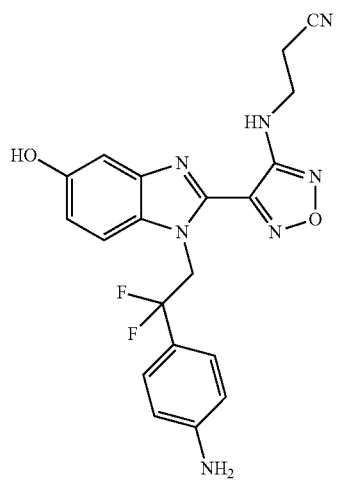 [SMILES: N#CCCNc1nonc1-c1nc2cc(O)ccc2n1CC(F)(F)c1ccc(N)cc1]
-continued
4
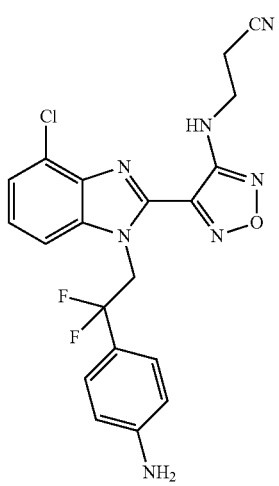 [SMILES: N#CCCNc1nonc1-c1nc2c(Cl)cccc2n1CC(F)(F)c1ccc(N)cc1]
5
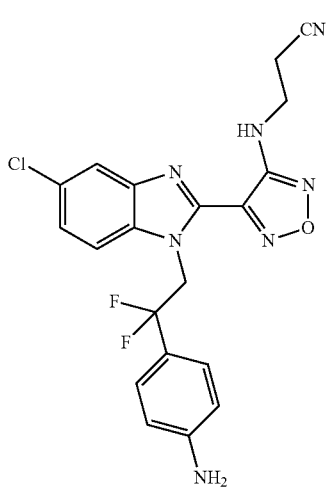 [SMILES: N#CCCNc1nonc1-c1nc2cc(Cl)ccc2n1CC(F)(F)c1ccc(N)cc1]
6
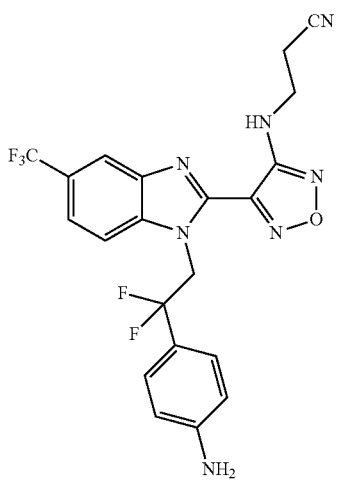 [SMILES: N#CCCNc1nonc1-c1nc2cc(C(F)(F)F)ccc2n1CC(F)(F)c1ccc(N)cc1]

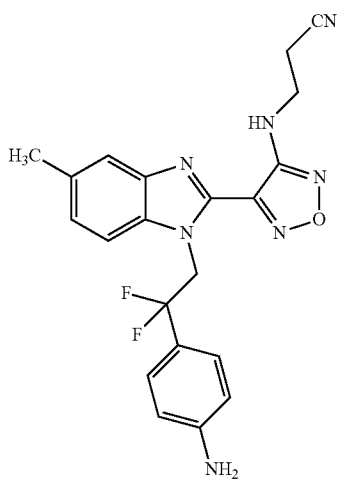 [SMILES: Cc1ccc2c(c1)nc(-c1nonc1NCCC#N)n2CC(F)(F)c1ccc(N)cc1]

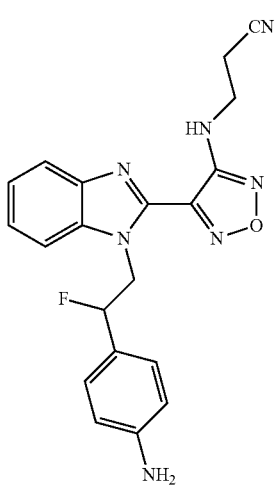

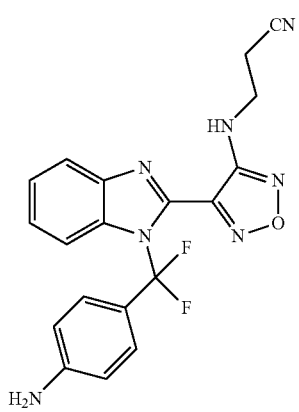 [SMILES: N#CCCNc1nonc1-c1nc2ccccc2n1C(F)(F)c1ccc(N)cc1]

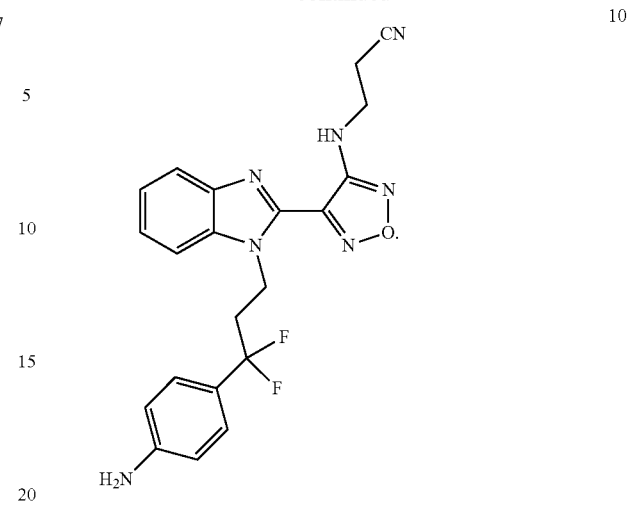

3. A pharmaceutical composition, comprising:
the benzimidazole derivative of claim 1, or an isomer, or a pharmaceutically-acceptable salt thereof; and
a pharmaceutically-acceptable carrier, a pharmaceutically-acceptable diluent, a pharmaceutically-acceptable excipient, or a combination thereof.

4. A method of preparing the benzimidazole derivative of claim 1, comprising:
(1) reacting compound (a) with acrylonitrile followed by purification to form compound (b);
(2) reacting the compound (b) with compound (c) in a first solvent in the presence of a base followed by purification to obtain compound (d);
(3) subjecting the compound (d) to fluorination in a second solvent in the presence of a fluorinating agent followed by purification to obtain compound (e), wherein the fluorinating agent is diethylaminosulfur trifluoride (DAST) or bis (2-methoxyethyl) aminosulfur trifluoride (BAST); and
(4) converting $R_2'$ in the compound (e) into $R_2$ in a third solvent followed by purification to obtain compound (I-1), as shown in the following reaction scheme:

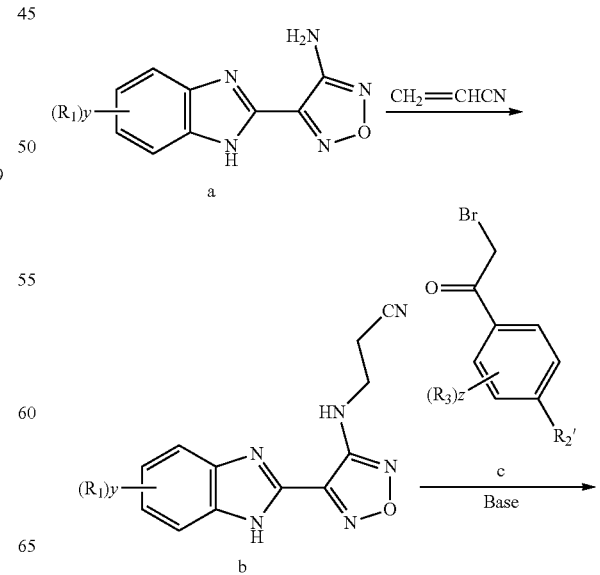

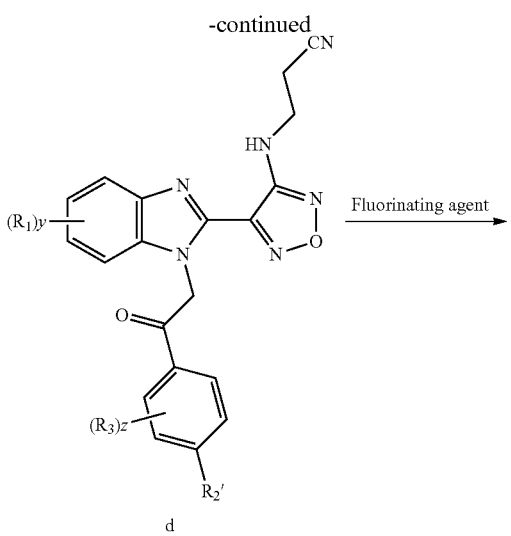

d

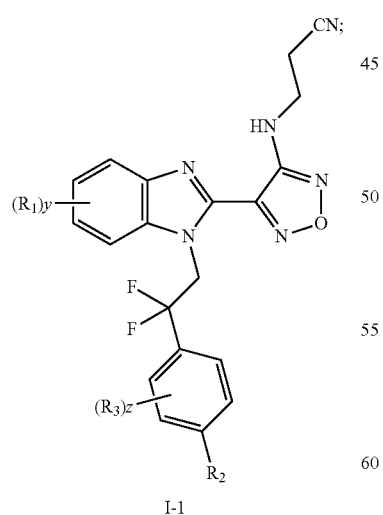

e

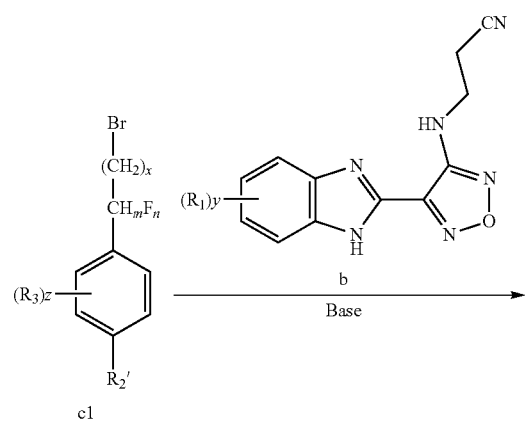

I-1 wherein $R_2'$ is nitro group or a protected amino group;
the base is an inorganic base or an organic base; wherein the inorganic base is selected from the group consisting of sodium hydroxide, potassium hydroxide, sodium hydride, calcium hydride, calcium fluoride, cesium fluoride, sodium carbonate, potassium carbonate, cesium carbonate, potassium phosphate and a combination thereof; and the organic base is selected from the group consisting of lithium diisopropylamide, butyl lithium, lithium bis(trimethylsilyl)amide, triethylamine, diisopropylethylamine, 1,8-diazabicyclo[5.4.0]undec-7-ene and a combination thereof;

the first solvent, the second solvent and the third solvent are independently a proton solvent, an aprotic solvent, or a mixture thereof;

steps (1)-(4) are independently performed at a temperature of −78-180° C.;

purifications in steps (1)-(4) are performed each independently by solvent extraction, precipitation, crystallization, column chromatography or a combination thereof; and in the column chromatography, a filler is a gel, macro porous resin, or aluminum oxide; and an eluent is a petroleum ether-acetone mixture, a petroleum ether-ethyl acetate mixture, or a petroleum ether-dichloromethane mixture.

5. The method of claim 4, wherein the first solvent, the second solvent and the third solvent are each independently dichloromethane, dichloroethane, tetrahydrofuran, acetonitrile, ethylene glycol dimethyl ether, N, N-dimethylformamide, or dimethyl sulfoxide.

6. A method of preparing the benzimidazole derivative of claim 1, comprising:

(1) reacting compound (b) with compound (c1) in a first solvent in the presence of a base followed by purification to produce compound (e1); and (2) converting $R_2'$ in the compound (e1) into $R_2$ in a second solvent followed by purification to obtain compound (I), as shown in the following reaction scheme:

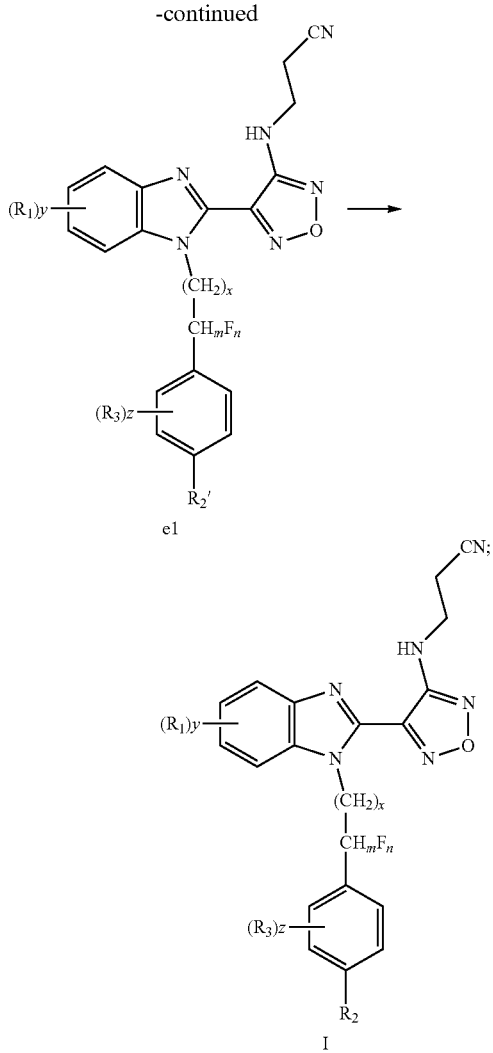

wherein R$_2$' is nitro group or a protected amino group;
the base is an inorganic base or an organic base; wherein the inorganic base is selected from the group consisting of sodium hydroxide, potassium hydroxide, sodium hydride, calcium hydride, calcium fluoride, cesium fluoride, sodium carbonate, potassium carbonate, cesium carbonate, potassium phosphate and a combination thereof; and the organic base is selected from the group consisting of lithium diisopropylamide, butyl lithium, lithium bis(trimethylsilyl)amide, triethylamine, diisopropylethylamine, 1,8-diazabicyclo[5.4.0]undec-7-ene and a combination thereof;

the first solvent and the second solvent are independently a proton solvent, an aprotic solvent, or a mixture thereof;

steps (1)-(2) are independently performed at a temperature of −78-180° C.;

purifications in steps (1)-(2) are performed each independently by solvent extraction, precipitation, crystallization, column chromatography or a combination thereof; and in the column chromatography, a filler is a gel, macro porous resin, or aluminum oxide; and an eluent is a petroleum ether-acetone mixture, a petroleum ether-ethyl acetate mixture, or a petroleum ether-dichloromethane mixture.

7. The method of claim 6, wherein the first solvent and the second solvent are each independently dichloromethane, dichloroethane, tetrahydrofuran, acetonitrile, ethylene glycol dimethyl ether, N, N-dimethylformamide, or dimethyl sulfoxide.

8. A method for treating a cancer in a subject in need thereof, comprising:
administering the benzimidazole derivative of claim 1, or an isomer, or a pharmaceutically-acceptable salt thereof to the subject;
wherein the cancer is selected from the group consisting of glioma, non-small cell lung cancer (NSCLC), colon cancer and breast cancer.

9. The method of claim 8, wherein the benzimidazole derivative, or an isomer, or a pharmaceutically-acceptable salt thereof is administered in combination with an anticancer agent.

10. The method of claim 9, wherein the anticancer agent is selected from the group consisting of adriamycin, bleomycin, vincristine, taxane, etoposide, 5-fluorouracil, cyclophosphamide, methotrexate, cisplatin, retinoic acid, temozolomide, actinomycin, imatinib, gefitinib, sorafenib, erlotinib, sunitinib, afatinib, cabozantinib, Osimertinib, rituximab, cetuximab, trastuzumab, nivolumab, pembrolizumab, atezolizumab, durvalumab, avelumab and a combination thereof.

* * * * *